(12) United States Patent
Bittner

(10) Patent No.: US 6,894,093 B2
(45) Date of Patent: May 17, 2005

(54) MATERIALS FREE OF ENDORINE DISRUPTIVE CHEMICALS

(76) Inventor: George D. Bittner, 5105 Evans, Suite 100, Austin, TX (US) 78751

( * ) Notice: Subject to any disclaimer, the term of this patent is extended or adjusted under 35 U.S.C. 154(b) by 0 days.

(21) Appl. No.: 10/143,385

(22) Filed: May 10, 2002

(65) Prior Publication Data

US 2003/0065061 A1 Apr. 3, 2003

Related U.S. Application Data

(60) Provisional application No. 60/290,595, filed on May 10, 2001.

(51) Int. Cl.[7] ................ C08F 110/02; C08F 110/06; C08K 5/04; C08K 5/16; C08K 5/36

(52) U.S. Cl. ............... 524/99; 524/81; 524/86; 524/104; 524/186; 524/284; 524/287; 524/299; 524/323; 524/334; 524/340; 524/543; 524/583; 524/585; 525/333.7; 525/333.9; 525/343; 525/375; 525/379; 525/384; 525/385; 525/386; 526/351; 526/352; 526/135; 526/204; 526/210; 526/213; 526/216; 526/234; 526/236

(58) Field of Search ................ 526/351, 352, 526/135, 204, 210, 213, 216, 234, 236; 524/81, 86, 99, 104, 186, 284, 287, 299, 323, 334, 340, 543, 583, 585; 525/333.7, 333.9, 343, 375, 379, 384, 385, 386

(56) References Cited

U.S. PATENT DOCUMENTS 4,824,885 A * 4/1989 Magni et al. ............ 524/120
6,448,315 B1 * 9/2002 Lidgren et al. ........... 524/110

FOREIGN PATENT DOCUMENTS

JP 2000-53116 * 2/2000
WO WO 00/49079 * 8/2000

OTHER PUBLICATIONS

Raloff, J., EcoCancers: Do environmental factors underlie a breast cancer epidemic?; Science News, Jul. 3, 1993, V. 144, No. 1, pp. 10–13, Washington, D.C., US, Abstract only.

Zhu, Dao–wei, et al.; Crystallogenesis of a human estradiol dehydrogenase–substrate complex; Journal of Crystal Growth, V. 168 No. 1–4, Oct. 2, 1996, pp. 275–279, Heroshima, Jpn, Abstract only.

Roberts, M., Denmark Considers PVC Phaseout, Chem. Week, Feb. 21, 1996, V. 158, No. 7, p. 17, Denmark, EU, Abstract only.

* cited by examiner

Primary Examiner—Roberto Rabago

(57) ABSTRACT

The present invention describes plastic materials and food additives that are free or substantially free from endocrine disruptive chemicals. The plastic materials may be used in products which are exposed to individuals in which endocrine disruptive activity is particularly disadvantageous, such as baby bottles, baby toys, food containers, medical containers, animal cages and medical products. The food additives may be used in food products that are ingested by individuals in which endocrine disruptive activity is particularly disadvantageous, such as newborns or the physically infirm. The present invention also describes a series of assays which, when performed in combination, provide a novel method for determining the presence of endocrine disruptive activity.

2 Claims, No Drawings

MATERIALS FREE OF ENDORINE DISRUPTIVE CHEMICALS

PRIORITY STATEMENT UNDER 35 U.S.C. § 119 & 37 C.F.R. § 1.78

This non-provisional application claims priority based upon prior U.S. Provisional Patent Application Ser. No. 60/290,595 filed May 10, 2001 in the name of George Bittner, entitled "Materials Void of Adverse Hormonal Activity and Method For Determining the Presence of Hormonally Active Substances in Materials."

FIELD

The present invention relates, generally, to the field of plastics and, more specifically, to plastic materials and food additives that are substantially free of endocrine disruptive chemicals. The present invention also relates to methods for detecting endocrine disruptive activity.

BACKGROUND

There is increasing evidence that certain synthetic and natural chemicals, called endocrine disruptors, may act as antagonists or antagonists to estrogens or androgens and may interfere in multiple ways with the action of thyroid hormones. For example, endocrine disruptors can mimic or block chemicals naturally found in the body, thereby altering the body's ability to produce hormones, interfering with the ways hormones travel through the body, and altering the concentration of hormones reaching hormone receptors. Although relatively few chemicals have been examined for their endocrine disruptive effect, those chemicals that have shown such an effect are increasingly found in common food and plastic products.

Endocrine disruptors include chemicals such as, for example, polychlorinated biphenyls (PCBs), dioxins and furans. These chemicals are found environmentally in insecticides, herbicides, fumigants, and fungicides that are used in agriculture as well as in the home. Other endocrine disruptors are found in common chemicals such as detergents, dental amalgams and resins that coat the inside of tin cans. In addition, research has found that, because the polymerization process used to make plastics is not complete, unpolymerized monomers with estrogenic activity can migrate out of plastics resulting in deleterious estrogenic, carcinogenic or toxic effects in humans and other species.

By way of example, di(2-ethylhexyl) phthalate (DEHP) is a plasticizer that is a colorless liquid with almost no odor. DEHP is commonly used in producing polyvinyl chloride (PVC) plastic products like toys, vinyl upholstery, shower curtains, adhesives, and coatings. PVC plastic may contain up to 40% DEHP. DEHP, an estrogen-mimicking chemical, has been found to leach from these plastics, thereby creating problems with the materials in contact with the plastic. For example, DEHP has been found to leach from intravenous bags and tubing into the blood and medications being administered to patients. Exposure to DEHP through intravenous bags and tubing presents a health risk that could be avoided through the use of a plastic material that does not contain endocrine disruptive chemicals.

Similarly, bisphenol A is a monomer used to synthesize a number of plastics, such as polycarbonates, epoxy, phenoxy and polysulfone polymers, and is released in significant amounts when these plastics are exposed to water, particularly when heated. Bisphenol A has been shown to possess deleterious estrogenic activity. Nevertheless, plastics manufactured with bisphenol A, such as polycarbonate, are commonly used for food and beverage containers, baby bottles, baby toys, microwaveable containers and medical items.

Molecular Mechanisms by Which Endocrine Disruptors Produce Estrogenic Activity

Endocrine disruptors and natural estrogens share a common mechanism of action. In normal cases, estrogenic activity is produced by binding natural estrogen to an estrogen receptor (ER) within the nucleus of the cell, followed by transcriptional activation of these occupied ERs. When endocrine disruptors are present, normal estrogenic activity is supplanted when endocrine disruptors bind an ER, causing transcriptional activation of the ER even though no natural estrogen is present. Similarly, antiestrogenic activity is produced by endocrine disruptors which bind to ERs but which do not subsequently activate the occupied ER. Finally, selective estrogen receptor modulators (SERMs) bind to ERs, but subsequently activate cellular responses that differ from those activated by the natural estrogens. In general, all but a very small number of molecules that bind to ERs produce some activation of the receptors, as either estrogens or as SERMs. In other words, there are several potential mechanisms by which food antioxidants and other chemicals produce endocrine disruptive activity, but the most common, and best understood, mechanism is via binding to estrogen receptors, thus mimicking the action of natural estrogens.

Effects of Endocrine Disruptors on Human Health

Researchers are exploring the possible link between exposure to endocrine disrupters and breast cancer, testicular cancer, and low sperm count. Deleterious estrogenic effects in humans occur at environmentally-relevant concentrations and include abnormal brain maturation leading to developmental problems or pathologies such as, for example, learning disabilities, attention disorders, abnormalities in motivation, emotion, cognitive development and reproduction, increases in aggressive behavior and changes in sexual orientation. Although the research regarding the effects of these chemicals on human health is just beginning, studies have already been completed on the effect of prenatal exposures to endocrine disruptors on child behavior that have documented developmental injury.

When tested in animal model systems, endocrine disruptors produce deleterious estrogenic effects at concentrations less than those concentrations that are released by certain plastics. For example, research has found that very low dosages of endocrine disruptors exhibit behavioral effects on rodents including, for example, learning disabilities, disorders of attention, motivation, emotion, cognitive development, and changes in sexual orientation and aggressive behavior. Other effects include alterations of reproductive organs of infant and adult males and females such as reduced sperm counts, prostate enlargement, ovarian and uterine dysfunction, and the rate of growth and time to sexual maturation.

As with many hormones, the effects described above are often more dramatic in fetal or developing mammals than in adults. In adults, hormones mainly regulate ongoing physiologic processes. As a result, adult bodies can sometimes compensate or recover from temporary hormonal modulation. Hormonal effects in the fetus are much more profound because they affect gene expression that governs development of organs as well as lifelong hormonal traits, such as receptor numbers and hormonal production. Accordingly, in the case of endocrine disruptors and other developmental toxicants, the timing of exposure may be more important than the dose.

Concern over the effects of endocrine disruptors has increased recently as a result of research showing that plastics commonly used in the home, such as, for example, baby products, food containers and microwaveable products, readily leach endocrine disruptive chemicals. The ubiquity of such plastic items almost certainly contributes to deleterious hormonal effects on human development, beginning prenatally and continuing through puberty and into adulthood. For example, recent data show that levels of bisphenol A in human umbilical cords are 0.2 to 2 micrograms/kg which is consistent with the levels of bisphenol A reported to leach from can linings and plastic baby bottles into vegetable products eaten by babies. Research has shown that a typical daily intake of 700 ml of formula containing 5 ppb bisphenol A from a baby bottle by a 7 kg baby would result in a daily dose of bisphenol A of 0.5 micrograms/kg/day. Furthermore, deleterious developmental changes have been reported in snails, fish, frogs, and rodents at 0.5 to 2 micrograms/kg/day. While it is unlikely that randomized trials will ever directly examine the deleterious developmental effects of bisphenol A on human infants, it is likely that such deleterious effects are produced in humans since basic endocrine mechanisms are not markedly different in rodents and humans.

In part as a response to the recent concern over the effects of endocrine disruptors, the United States government and foreign governments have become active in the testing and regulation of endocrine disruptors. In the United States, the Food Quality Protection Act of 1996 requires that the United States Environmental Protection Agency to develop an endocrine disruptor screening program. The Safe Drinking Water Act of 1996 authorizes the United States Environmental Protection Agency to screen endocrine disruptors found in drinking water. Outside the United States, a number of countries have adopted regulations of endocrine disruptors. For example, the European Union banned the use of phthalates and PVC, known endocrine disruptors, in toys for children under three years of age.

Plastic Monomers and Additives

Plastics are made from monomers that are synthesized into polymers, typically by the application of heat, pressure and, in certain cases, catalysts. The most common monomers from which plastics are made are shown in Table 1.

Of the monomers used to produce common plastics, polyethylene (PE) is most frequently used because it is inexpensive to synthesize and has extremely versatile properties. Low density PE (LDPE) and linear low density PE (LLDPE) are also widely used, predominantly for extruded materials and film materials which are commonly used to wrap food products. High density PE (HDPE) is used in applications that involve contact with either food products or potable water, such as, for example, film, plastic bottles, and plastic pipe. Many plastic containers for carbonated beverages are now made of polyethylene terephthalate (PET), an excellent barrier material against the migration of carbon dioxide through the container.

Numerous additives are introduced after the synthesis of plastics to enhance their properties. For example, antioxidants are added to increase the useful life of PE and other plastics by preventing, or at least minimizing, the degradation of oxygen which can often cause breakage of molecular chains leading to other undesirable effects such as, for example, discoloration, loss of surface gloss, surface cracking, and lowering of tensile strength. Furthermore, plastics are typically processed into useful shapes at temperatures in excess of 150° centigrade which can lead to thermo-oxidative degradation of molecular weight, ductility, and strength. Table 2 lists some common antioxidants, all of which, with the possible exception of organo-hosphites and thio-ethers, have estrogenic, carcinogenic or other toxic effects.

TABLE 2

Some Common Antioxidants

| Antioxidants | Predicted Estrogenic Activity | Predicted Carcinogenic or Other Toxic Effects |
|---|---|---|
| (di)Butyl hydroxy toluene (BHT) | Yes | Yes |
| Hindered Phenols | Yes | NT |
| Organo-Phosphites | NT | NT |
| Thio-esters | NT | NT |
| 2° Acrylamines | NT | Yes |

Sources for Table 2: EDSTAC, 1998; NRC, 1999; NTP, 2000; Society for Plastics Industry.
NT—To Applicant's knowledge this chemical has not yet been tested for estrogenic activity.

TABLE 1

Plastic Production

| Monomer | Polymer | Acronym | Monomer Exhibits Estrogenic (EA) or Carcinogenic (CA) Activity |
|---|---|---|---|
| Ethylene | Polyethylene | PE[2] (LDPE, HDPE, LLDPE) | NT |
| Vinylchloride | Polyvinylchloride | PVC | CA |
| Propylene | Polypropylene | PP | NT |
| Styrene | Polystyrene | PS | NT |
| Bisphenol A | Polycarbonate[1,3] (Epoxy, Polysulfone, Phenoxy, etc Polymers) | PC | EA |
| Terephthalic acid + ethylene glycol | Polyethylene, terephthalate | PET | EA |

Sources for Table 1: EDSTAC, 1998; NRC, 1999; NTP, 2000; Society for Plastics Industry.
NT—To Applicant's knowledge this chemical has not yet been tested for estrogenic activity.
[1]Polymer can be formulated to produce plastics with vastly different characteristics.
[2]PE can be synthesized into low-density PE (LDPE), high-density polyethylene (HDPE), and linear low-density PE (LLDPE).
[3]Monomers are incompletely polymerized and may migrate out of the final plastic product.

Depending on the material and its desired use, additives other than antioxidants are also used in plastic processing. For example, various pigments including, for example, lead chromates, lead molybdates, lead sulphteranges, chromium oxides, ferric ammonium ferrocyanide, carbon black and phthalo blues are used to add color to PE and other polymers. Common pigments are found in Table 3. Many of these pigments exhibit endocrine disruptive activity or other toxic effects.

TABLE 3

Some Common Pigments

| Pigments | Predicted Estrogenic Activity | Predicted Carcinogenic or Other Toxic Effects |
| --- | --- | --- |
| Lead chromate | | Yes |
| Lead molybdate | | Yes |
| Lead sulphterange | | Yes |
| Chromium oxides | | Yes |
| Ferric ammonium | | Yes |
| Ferrocyanide | | Yes |
| Carbon black | | No |
| Phthalo blues | Yes | |

Sources for Table 3: EDSTAC, 1998; NRC, 1999; NTP, 2000, Society for Plastics Industry.

Other classes of plastic additives include plasticizers and stabilizers. For example, esters of phthalic acid, one of the most ubiquitous plasticizers for PVC compounds, all exhibit estogenic disruptive activity and are frequently used in high concentrations, often 40–80% by weight, in plastic materials. This is extremely troublesome because most plasticizers are quite mobile at ambient conditions and, when child-oriented products are made from these materials, children may ingest significant amounts of these compounds when they "taste" their surroundings.

Stabilizers on the other hand, inhibit or reduce damage caused by electromagnetic radiation to PEs and other polymers. Thermal stabilizers for PVC include barium-cadmium soaps, organo-tin compounds, lead compounds, and cadmium-zinc soap. Additives that contain lead and cadmium are clearly toxic. Many of the most common ultraviolet stabilizers for PE such as, for example, benzothiazoles and benzophenones have exhibited endocrine disruptive activity and have rather low molecular weight. Such low molecular weight (1000 daltons) stabilizers are routinely added to PE and are sufficiently mobile to migrate by diffusion from the plastic to the environment. Common stabilizers are found in Table 4.

TABLE 4

Some Common Stabilizers

| Stabilizers | Predicted Estrogenic Activity | Predicted Carcinogenic or Other Toxic Effects |
| --- | --- | --- |
| Barium-cadmium soaps | | Yes |
| Organo-tin compounds | | No |
| Lead compounds | | Yes |
| Cadmium-zinc soaps | | Yes |
| Benzothiazoles | Yes | |
| Benzophenones | Yes | |

Sources for Table 4: EDSTAC, 1998; NRC, 1999; NTP, 2000; Society for Plastics Industry.

Some plastic additives are widely used in the United States in spite of their known endocrine disruptive activity. For example, bisphenol A is a monomer used to synthesize various plastics such as, for example, PCs, epoxy, phenoxy, and polysulfone polymers and is released in significant amounts when the polymer is exposed to water, particularly when heated. Although bisphenol A has been demonstrated to exhibit endocrine disruptive activity, PC products are commonly used for food and beverage containers, baby bottles, baby toys, microwaveable containers, and medical items. PC production has rapidly increased in the United States and, consequently, bisphenol A is now one of the top 50 chemicals produced in the U.S.

Due to federal regulations and commercial concerns, most monomers or additives with carcinogenic or other lethally toxic effects are not found in plastics routinely contacted by humans or that contact food. The U.S. Food and Drug Administration (FDA) has long recognized the problem of migration of chemicals out of plastics and other products and has strictly regulated the antioxidants and other agents in plastic compounds that contact food. The FDA has required that such additives be tested for carcinogenic properties and other acute toxic effects. Less toxic stabilizers such as tin soaps are approved by the FDA for food contact, but less expensive, albeit toxic, stabilizers such as, for example, barium, cadmium, and lead compounds, are approved for use in other applications such as electronics parts that do not contact food. Although tested for carcinogenic activity and acute toxicity, chemicals used in plastics that contact humans directly or that contact food have not been tested for estrogenic activity and, as a result, the disruptive activity has not yet been regulated. Furthermore, the formulations used to manufacture plastics usually are not required to be revealed to other companies, consumers or governmental agencies. Even when the manufacturer divulges the primary monomer or polymer used in a plastic, it rarely reveals all additives used in the formulation.

The United States Food Quality Protection Act requires that chemicals be tested and regulated for endocrine disruptive activity. In furtherance thereof, a multimillion-dollar request for proposal for validation of tests on endocrine disruptive activity has recently been awarded by the U.S. Environmental Protection Administration. The need for, and regulation of, safer plastics with less endocrine disruptive activity is now being driven by well-documented scientific findings.

Numerous products have been affected by regulations or consumer concerns in other developed countries. For example, several European Union countries recently banned the use of phthalates and PVC plastics in toys for children under three. Consequently, plastic bottles or teething rings in Europe, Japan and the U.S. are no longer made from PVC due to concerns by the public and commercial retailers about the deleterious health effects of phthalates and PVC. As a second example, the use of many PC products such as, for example, baby bottles and dishes, has recently decreased dramatically in Japan due to public awareness that these PCs release bisphenol A whose estrogenic activity has potentially deleterious effects on reproductive functions and many other physiological systems in humans.

Although the concern over the presence of endocrine disruptive chemicals in plastics is escalating, no plastic product on sale in the United States or international market has been demonstrated to be free of endocrine disruptive chemicals. Therefore, the need remains for a plastic material that is substantially free of endocrine disruptive chemicals.

Food Additives

More than 2,800 different food additives are routinely used to maintain product freshness and quality and help retard physical, chemical and biological deterioration. Table 5 lists some commonly used food additives and their intended function.

TABLE 5

Commonly Used Food Additives and Intended Function

| Additive | Intended function | Examples |
|---|---|---|
| Antimicrobial preservatives | Prevent microbial growth | Sodium benzoate, calcium propionate, potassium sorbate, sodium nitrite |
| Antioxidants | Prevent rancidity | BHT, BHA, propyl gallate, tocopherols |
| Flavor enhancers | Supplement, enhance or modify original flavor | MSG, disodium inosinate, disodium guanylate |
| Synergists | Increase the effects of other food additives | Citric acid, tricalcium phosphate and other phosphates, ascorbic acid |

Antioxidants are one of the most important and most widely used food additives. The oldest and most common antioxidants that are deemed suitable for food contact service belong to a class of materials known as hindered phenols. The most ubiquitous of these is BHT. Since 1949, BHT has been widely used as an antioxidant food additive in large part because it is very inexpensive and because it was routinely assumed to be non-toxic. BHT works by intercepting and reducing free radicals that are associated with the oxidation process. However, primary data suggests that BHT exhibits endocrine disruptive activity. BHT is therefore almost certainly unsuitable as an antioxidant in foods.

Table 6 lists 12 common food antioxidants. Some antioxidants such as, for example, BHA, BHT, tocopherols, TBHQ, gallates and THBP, are widely used due to their overall efficacy. Others are "natural" antioxidants isolated from plants, although they are less commonly used in the manufacture of food products at present. The estrogenic activity of food antioxidants has not yet been examined, but many food antioxidants would be expected to exhibit estrogenic activity because they contain a phenolic ring. Since many estrogenic chemicals have effects at picomolar to nanomolar levels and antioxidants are often added to foodstuffs in micromolar to millimolar concentrations (i.e. 1000× greater), such estrogenic antioxidants could be a significant health hazard, particularly to a developing fetus. The need exists, therefore for food additives substantially free of endocrine disruptive activity.

TABLE 6

Antioxidants Permitted in Foods in the United States

| Primary Antioxidants | # of Benzene Rings[A] | # —OH[B] (on benz) | QSAR[C] RBA | Use or Origin | ADI[D] Approved |
|---|---|---|---|---|---|
| 1. Butylated hydroxyanisole (BHA) | 1 | 1 (1) | yes, −5 | Fats and oils, confectioneries, food-coating material, and | 0–0.5 mg/kg 0.01–0.1% |
| 2. Butylated hydroxytoulene (BHT) | 1 | 1 (1) | yes, −5 | Low fat foods, fish products, packaging materials[6] | 0–0.125 mg/kg 0.005–0.02% |
| 3. Tocopherols | 1 | 1 (1) | yes | Major lipid soluble antioxidant | 0.15–2 mg/kg |
| 4. Tert-Butylhydroquinone (TBHQ) | 1 | 2 (2) | yes | Stabilizes fats, oils, confectionery products, etc | 0–0.2 mg/kg |
| 5. Propyl gallate | 1 | 3 (3) | no | Stabilizes animal fats and vegetable oils, meat products, spices and snacks | 0–2.5 mg/kg 0.001– 0.01%; 0.1% (chewing gum base) |
| 6. 2,4,5-Trihydroxy-butyrophenone (THBP) | 1 | 3 (3) | no | Stabilizes Vitamin A, oils, used in packaging material[6] | 0.02% Migration < 0.005% |
| 7. Curcumin[E] | 2 | 2 (2) | yes | from tumeric | |
| 8. Catechin[E] | 2 | 4 (4) | yes, −2.10 | from tea | |
| 9. Sesamin[E] | 2 | 0 (0) | ? | from sesame seeds | |
| 10. Sesamolin[E] | 2 | 0 (0) | ? | from sesame seeds | |
| 11. Carnosine[E] | 0 | 1 (0) | ? | from rosemary | |
| 12. Glycyrrhizic Acid[E] | 0 | 4 (0) | ? | from licorice | |

[A]# of benzene rings in this antioxidant.
[B]Number of —OH groups (number of —OH groups on benzene rings) in this antioxidant.
[C]yes, no: prediction of significant binding ability based only on number of OH and number of OH groups on benzene rings above; −#: Negative log relative ERα binding affinity (RBA) with respect to 17β-estradiol (RBA = 0) according to preliminary data calculated by a complete QSAR analysis. An antioxidant with an ERα RBA more negative than −6 should have little or no ability to bind to ERα or ERβ.
[D]ADI: Average Daily Intake gives the recommended daily dietary allowance for these antioxidants.
[E]Good toxicological data does not exist for these "natural" antioxidants.
[F]Antioxidants may be added directly to packaging materials rather than the food product itself. The effectiveness of the antioxidant depends on its rate of migration to the food material and the antioxidant vapor pressure. Breakfast cereals and bakery goods are often packaged in this manner, permitting larger quantities of antioxidants to be added to the package liner, provided no more than the legally allowed concentrations migrate into the product.

Testing

The process of obtaining an approval for food additives for human use is regulated by Center for Food Safety and Applied Nutrition (CFSAN) at the FDA under the Federal Food Drug and Cosmetic Act. The required toxicological studies include absorption, metabolism, and excretion studies, acute toxicity, short-term studies, long-term and carcinogenicity studies, reproduction, skin toxicity, and mutagenicity. Some of the additional recommended studies include neurotoxicity and immunotoxicity. Despite the extensive number of studies required by CFSAN, the current toxicological studies do not adequately address endocrine disruptor issues, in part because the endpoint measurements and the doses at which LD50 or carcinogenic effects and endocrine disruptive effects are observed are markedly different and in part because different assays are needed.

A vast majority of the 80,000 chemicals currently sold on the U.S. and international market have not been tested for estrogenic effects. One significant reason for the lack of testing has been the lack of a reliable test procedure for testing the presence of endocrine disruptive activity. The need exists, therefore for a reliable, comprehensive test for the presence of endocrine disruptors in plastics and foods.

Unique/Innovative Approach in Development of New Plastic Formulations

As discussed above, plastics synthesized from bisphenol A, such as polycarbonate and other plastics, have deleterious estrogenic activity, but are now commonly used for food and beverage containers, baby bottles, baby toys, microwaveable containers, and medical items. Hence, there is a demand for new plastic formulations that lack biologically detectable estrogenic activity but retain the useful characteristics of current plastics.

In one embodiment of the present invention, a monomer is polymerized to form a polymeric material that is substantially void of endocrine disruptive chemicals. This polymeric material may be, for example, polyethylene or polypropylene. Articles may be made form this polymeric material such as, for example, baby bottles, baby toys, medical devices, food containers, beverage containers, medical containers and animal cases.

In another embodiment of the present invention, a monomer is polymerized to form a polymeric material, such as polyethylene or polypropylene, with the addition of only an antioxidant known not to contain endocrine disruptive materials such as, for example, propyl gallate, octyl gallate, dodecyl gallate, ethoxyquin, carnosine, glycyrrhizic acid, sesamin, sesamolin, monoisopropyl citrate and thiodiproprionic acid. Once again, an article such as that described in the foregoing paragraph may be made from this material.

Polymeric materials substantially void of endocrine disruptive chemicals may be prepared by processing, for example, an ethylene monomer with itself to form a polyethylene polymer and subsequently converting that polyethylene polymer into the desired material such as, for example, an extruded film or other material. Similarly, a propylene monomer may be processed with other propylene monomers to form similar articles. In another embodiment, polymeric materials substantially void of endocrine disruptive chemicals may be prepared by polymerizing, for example, an ethylene monomer with an antioxidant known not to contain endocrine disruptive materials such as, for example, propyl gallate, dodecyl gallate, ethoxyquin, carnosine, glycyrrhizic acid, sesamin, sesamolin, monoisopropyl citrate and thiodiproprionic acid to form a polyethylene material and subsequently converting that polyethylene polymer into the desired material such as, for example, an extruded film or other article. A propylene monomer can be substituted for the ethylene monomer in the foregoing example to create a polypropylene material substantially free of endocrine disruptive materials.

The already daunting task of developing these new plastic formulations is made more complex by fact that the chemistry of effective additives that lack detectable estrogenic activity has not yet been explored. The development of new formulations that are commercially attractive and that lack biologically detectable estrogenic activity requires innovative combinations of scientific knowledge from several disparate scientific fields: endocrine physiology, molecular biology, environmental health science and polymer chemistry. The only way for to reliably determine that plastic formulations do not have biologically detectable estrogenic activity is for all chemicals in a plastic formulation, as well as those chemicals which leach from the plastic, to test negative for such activity in a series of state-of-the-art assays. The only way to determine the effectiveness of any additives lacking detectable estrogenic activity is to perform shelf life, or durability, studies, perhaps in combination with additional studies on plastic sheets that are exposed to harsh conditions such as extreme temperature, UV and microwave radiation, and chlorine exposure.

SUMMARY

The present invention relates, generally, to the field of plastics and, more specifically, to plastic materials and food additives that are substantially free of endocrine disruptive chemicals. Specifically, the present invention provides for the use of certain monomers, or the combination of certain monomers and additives, to make plastic compositions and products which are substantially free of endocrine disruptive chemicals and are therefore useful in products and applications where no endocrine disruptive effects are desired.

The present invention also relates to the field of food products and food additives and, more specifically, to food products and food additives that are substantially free of endocrine disruptive chemicals.

The present invention also relates to methods for detecting endocrine disruptive activity and, more specifically, to a series of assays which, when performed in combination, provide a novel method for determining the presence of endocrine disruptive activity.

What is claimed is:

1. A polymeric material substantially void of endocrine disruptive chemicals comprising a polymerized monomer wherein said monomer is polymerized in the presence of an antioxidant to form a polymeric material substantially void of endocrine disruptive chemicals, and wherein said antioxidant is selected from the group consisting of propyl gallate, octyl gallate, dodecyl gallate, ethoxyquin carnosine, glycyrrhizic acid, sesamin, sesamolin, monoisopropyl citrate and thiodiproprionic acid.

2. A process for preparing a polymeric material substantially void of endocrine disruptive chemicals, said process comprising the steps of: (a) polymerizing a monomer selected from the group consisting of ethylene and propylene; and (b) processing said polymerized monomer with an antioxidant to form a polymeric material substantially void of endocrine disruptive chemicals, wherein said antioxidant is selected from the group consisting of ethoxyquin, carnosine, glycyrrhizic acid, sesamin, sesamolin, monoisopropyl citrate and thiodiproprionic acid.

* * * * *

UNITED STATES PATENT AND TRADEMARK OFFICE
CERTIFICATE OF CORRECTION

PATENT NO. : 6,894,093 B2  Page 1 of 1
APPLICATION NO. : 10/143385
DATED : May 17, 2005
INVENTOR(S) : George D. Bittner It is certified that error appears in the above-identified patent and that said Letters Patent is hereby corrected as shown below:

Title Page, item 54, the title should read --endocrine-- replacing "endorine".

Column 1, line 1, the title should read --endocrine-- replacing "endorine".

Signed and Sealed this

Eighth Day of August, 2006

JON W. DUDAS
*Director of the United States Patent and Trademark Office*